US007419666B1

(12) United States Patent
Iliaki et al.

(10) Patent No.: US 7,419,666 B1
(45) Date of Patent: Sep. 2, 2008

(54) TREATMENT OF OCULAR DISORDERS

(75) Inventors: Eirini Iliaki, Boston, MA (US); Anthony P. Adamis, Bronxville, NY (US); Joan W. Miller, Winchester, MA (US); Evangelos S. Gragoudas, Lexington, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 388 days.

(21) Appl. No.: 11/064,058

(22) Filed: Feb. 23, 2005

Related U.S. Application Data

(60) Provisional application No. 60/547,156, filed on Feb. 23, 2004.

(51) Int. Cl.
*A61K 39/395* (2006.01)
*C07K 16/28* (2006.01)

(52) U.S. Cl. .............. 424/144.1; 424/130.1; 424/143.1; 530/387.1; 530/388.22

(58) Field of Classification Search ........................ None
See application file for complete search history.

(56) References Cited

U.S. PATENT DOCUMENTS

| | | | |
|---|---|---|---|
| 5,871,734 | A | 2/1999 | Lobb et al. |
| 5,888,507 | A | 3/1999 | Burkly |
| 5,932,214 | A | 8/1999 | Lobb et al. |
| 6,291,511 | B1 | 9/2001 | Durette et al. |
| 6,465,513 | B1 | 10/2002 | Grant et al. |
| 6,479,492 | B1 | 11/2002 | Konradi et al. |
| 6,492,372 | B1 | 12/2002 | Konradi et al. |
| 6,495,525 | B1 | 12/2002 | Lee et al. |
| 6,524,581 | B1 | 2/2003 | Adamis |
| 6,545,003 | B1 | 4/2003 | Grant et al. |
| 6,559,127 | B1 | 5/2003 | Dappen et al. |
| 6,583,139 | B1 | 6/2003 | Thorsett et al. |
| 6,586,602 | B2 | 7/2003 | Thorsett et al. |
| 6,602,503 | B1 | 8/2003 | Lobb et al. |
| 6,608,101 | B1 | 8/2003 | Ni et al. |
| 6,630,512 | B2 | 10/2003 | Adams et al. |
| 6,685,617 | B1 | 2/2004 | Blinn et al. |
| 6,686,350 | B1 | 2/2004 | Zheng et al. |
| 6,852,878 | B2 | 2/2005 | Meng et al. |
| 6,903,088 | B2 | 6/2005 | Konradi et al. |
| 7,026,501 | B2 | 4/2006 | Kawaguchi et al. |
| 7,157,086 | B2 | 1/2007 | Lobb et al. |

OTHER PUBLICATIONS

Martin et al. (2005). Administration of a peptide inhibitor of alpha4-integrin inhibits the development of experimental autoimmune uveitis. Invest. Ophthalmol. Vis. Sci. 46(6):2056-2063.*
Hafezi-Moghadam et al. (2007). VLA-4 blockade suppresses endotoxin-induced uveitis: in vivo evidence for functional integrin up-regulation. FASEB J. 21(2):464-474.*

Albertini et al. (1998) "Elevated Concentrations of Soluble E-Selectin and Vascular Cell Adhesion Molecule-1 in NIDDM: Effects of intensive insulin treatment," Diabetes Care 21(6): 1008-13.

Bai et al. (2003) "Increased expression of intercellular adhesion molecule-1, vascular cellular adhesion molecule-1 and leukocyte common antigen in diabetic rat retina," Yan Ke Xue Bao 19(3): 176-83.

Barile et al. (1999) "Soluble cellular adhesion molecules in proliferative vitreoretinopathy and poliferative diabetic retinopathy," Curr. Eye Res. 19(3): 219-27.

Barouch et al. (2000) "Integrin-Mediated Neutrophil Adhesion and Retinal Leukostasis in Diabetes," Invest. Ophthalmol. Vis. Sci. 41: 1153-58.

Beck et al. (1993) "Optic Neuritis Treatment Trial," Arch. Ophthalmol. 111: 773-775.

Berson et al. (1993) "A Randomized Trial of Vitamin A and Vitamin E Supplementation for Retinitis Pigmentosa," Arch. Ophthalmol. 111: 761-772.

Boerner et al. (1991) "Production of antigen-specific human monoclonal antibodies from in vitro-primed human splenocytes," J. Immunol. 147: 86-95.

Brinchmann-Hansen et al. (1992) "Blood glucose concentrations and progression of diabetic retinopathy: the seven year results of the Oslo study," BMJ 304(6818): 19-22.

Devine et al. (1996) "Role of LFA-1, ICAM-1, VLA-4 and VCAM-1 in lymphocyte migration across retinal pigment epithelial monolayers in vitro," Immunology 88(3): 456-62.

DRS Coordinating Center, Dept. of Epidemiol. and Prevent Medicine (1981) "Photocoagulation Treatment of Proliferative Diabetic Retinopathy: Relationship of Adverse Treatment Effects to Retinopathy Severity: Diabetic Retinopathy Study Report No. 5," Dev. Ophthal. 2: 248-261.

DRS Research Group (1981) "Photocoagulation Treatment of Proliferative Diabetic Retinopathy: Clinical Application of Diabetic Retinopathy Study (DRS) Findings, DRS Report No. 8," Ophthalmol. 88(7): 583-600.

Fasching et al. (1996) "Elevated concentrations of circulating adhesion molecules and their association with microvascular complications in insulin-dependent diabetes mellitus," J. Clin. Endocrinol. Metab. 81(12): 4313-17.

Fryer et al. (1997) "Antibody to VLA-4, but not to L-selectin, protects neuronal M2 muscarinic receptors in antigen-challenged guinea pig airways," J. Clin. Invest. 99: 2036-44.

Ghosh et al. (2003) "Natalizumab for Active Crohn's Disease," N. Eng. J. Med. 348(1): 24-32.

(Continued)

*Primary Examiner*—Christine J Saoud
*Assistant Examiner*—Jon M Lockard
(74) *Attorney, Agent, or Firm*—Goodwin Procter LLP

(57) ABSTRACT

The invention includes a method of treating an intraocular disorder in a mammal, the method comprising administering to the mammal a Very Late Antigen-4 (VLA-4) antagonist for the treatment of selected ocular disorders.

48 Claims, No Drawings

OTHER PUBLICATIONS

Hernandez (2001) "Vitreous levels of vascular cell adhesion molecule and vascular endothelial growth factor in patients with proliferative diabetic retinopathy: a case-control study," Diatetes Care 24(3): 516-21.

Hynes et al. (2002) "Integrins: bidirectional, allosteric signalling machines," Cell 110: 673-687.

Kado et al. (1999) "Circulating intercellular adhesion molecule-1, vascular cell adhesion molecule-1, and E-selectin in patients with type 2 diabetes mellitus," Diabetes Res. Clin. Pract. 46(2): 143-48.

Karma et al. (1988) "Course and Outcome of Ocular Sarcoidosis," Amer. J. Ophthalmol. 106: 467-472.

Kim et al. (2001) "Vascular endothelial growth factor expression of intercellular adhesion molecule 1 (ICAM-1), and E-selectin through nuclear factor-kappa B activation in endothelial cells," J. Biol. Chem. 276(10): 7614-7620.

Kumar et al. (2001) "Targeting of vasculature in cancer and other angiogenic diseases," Trends Immunol. 22(3): 129.

Kuppner et al. (1993) "Adhesion molecule expression in acute and fibrotic sympathetic ophthalmia," Curr. Eye Res. 12(10): 923-934.

La Heij et al. (1998) "Adhesion molecules in iris biopsy specimens from patients with uveitis," Br. J. Ophthalmol. 82: 432-437.

Limb et al. (1996) "Distribution of TNF alpha and its reactive vascular adhesion molecules in fibrovascular membranes of proliferative diabetic retinopathy," Br. J. Ophthalmol. 80(2): 168-73.

Limb et al. (1999) "Vascular adhesion molecules in vitreous from eyes with proliferative diabetic retinopathy," Invest Ophthalmol. Vis. Sci. 40(10): 2453-57.

Lutty et al. (1997) "Relationship of polymorphonuclear leukocytes to capillary dropout in the human diabetic choroid," Am. J. Pathol. 151(3) 707-714.

Macular Photocoagulation Study Group (1982) "Argon Laser Photocoagulation for Senile Macular Degeneration: Results of a Randomized Clinical Trial," Arch. Ophthalmol. 100: 912-918.

Martin et al. (2005) "Administration of a peptide inhibitor of alpha4-integrin inhibits the development of experimental autoimmune uveitis," Invest Ophthalmol. Vis. Sci. 46(6): 2056-63.

Matsumoto et al. (2002) "Comparison of serum concentrations o fsoluble adhesion molecules in diabetic microangiopathy and macroangiopathy," Diabet. Med. 19(10) 822-826.

McLeod et al. (1995) "Enhanced expression of intracellular adhesion molecule-1 and P-selectin in the diabetic human retina and choroid," Am. J. Pathol. 147(3): 642-653.

Melder et al. (1996) "During angiogenesis, vascular endothelial growth factor and basic fibroblast growth factor regulate natural killer cell adhesion to tumor andothelium," Nat. Med. 2(9) 992-997.

Miller et al. (2003) "A Controlled Trial of Natalizumab for Relapsing Multiple Sclerosis," N. Eng. J. Med. 348(1): 15-22.

Miyamoto et al. (1998) "In vivo demonstration of increased leukocyte entrapment in retinal microcirculation of diabetic rats," Invest Ophthalmol. Vis. Sci. 39(11): 2190-94.

Miyamoto et al. (1999) "Prevention of leukostasis and vascular leakage in streptozotocin-induced diabetic retinopathy via intercellular adhesion molecule-1 inhibition," PNAS USA 96(19) 10836-41.

Olson et al. (1997) "Soluble leucocyte adhesion molecules in diabetic retinopathy stimulate retinal capillary endothelial cell migration," Diabetologia 40(10): 1166-71.

Penfold et al. (1984) "An ultrastructural study of the role of leucocytes and fibroblasts I nthe breakdown of Bruch's membrane," Austral. J. Ophthamol. 12: 23-31.

Penfold et al. (1985) "Senile Macular Degeneration: The involvement of immunocompetent cells," Graefe's Arch. Clin. Exp. Ophthalmol. 223: 69-76.

Penfold et al. (1987) "Age-related macular degeneration: ultrastructural studies of the relationship of leucocytes to angiogenesis," Graefes Arch. Clin. Exp. Ophthalmol. 225(1): 70-76.

Pulido et al. (1991) "Functional evidence for three distinct and independently inhibitable adhesion activities mediated by the human integrin VLA-4. Correlation with distinct alpha 4 epitopes," J. Biol. Chem. 266(16): 10241-45.

Reddy et al. (1995) "Distribution of Growth Factors in Subfoveal Neovascular Membranes in Age-Related Macular Degeneration and Presumed Ocular Histoplasmosis Syndrome," Amer. J. Ophthalmol. 120: 291-301.

Rothova (2002) "Corticosteroids and Uveitis," Ophthalmol. 15: 389-94.

Schmidt-Erfurth et al. (1999) "Photodynamic therapy with verteporfin for choroidal neovascularization caused by age-related macular degeneration: results of retreatments in a phase 1 and 2 study," Arch. Ophthalmol. 117(9):1177-87.

Schroder et al. (1991) "Activated monocytes and granulocytes, capillary nonperfusion, and neovascularization in diabetic retinopathy," Am. J. Pathol. 139(1): 81-100.

Seregard et al. (1994) "Immunohistochemical characterization of surgically removed subfoveal vascular membranes," Graefes Arch. Clin. Exp. Ophthalmol. 232(6): 325-329.

Springer et al. (1994) "Traffic signals for lymphocyte recirculation and leukocyte emigration. The multistep paradigm." Cell 76: 301-314.

Tang et al. (1994) "Expression of intercellular adhesion molecule-1 (ICAM-1) and vascular cell adhesion molecule-1 (VCAM-1) on proliferating vascular endothelial cells in diabetic epiretinal membranes," Br. J. Ophthalmol. 78(5): 370-6.

Tang et al. (1994) "Proliferation and activation of vascular endothelial cells in epiretinal membranes from patients with proliferative diabetic retinopathy. An immunohistochemistry and clinical study," Ger. J. Ophthalmol. 3(3): 131-6.

von Andrian et al. (2003) "Alpha-4 integrins as Therapeutic Targets in Autoimmune Disease," N. Eng. J. Med. 348(1): 68-72.

von Andrian et al. (2000) "Review Article, Advances in Immunology—T-Cell Function and Migration: Two Sides of the Same Coin," NEJM 343(14): 1020-1034.

Xu et al. (2003) "Leukocyte Trafficking in Experimental Autoimmune Uveitis: Breakdown of Blood-Retinal Barrier and Upregulation of Cellular Adhesion Molecules," IOVS 44(1): 226-234.

Yoshizawa et al. (1998) "Elevated serum levels of soluble vascular cell adhesion molecule-1 in NIDDM patients with proliferative diabetic retinopathy," Diabetes Res. Clin. Pract. 42(1): 65-70.

NCBI Report for Ref. Seq. NP_001069 [gi:4507875], Vascular Cell Adhesion Molecule 1 Isoform Precursor [*Homo sapiens*] (4 pages) and printout of sequence revision history (2 pages), from NCBI web site at www.ncbi.nlm.nih.gov (printed Jan. 20, 2008).

NCBI Report for Ref. Seq. NP_002017 [gi:1933542], fibronection 1 isoform 3 preproprotein [*Homo sapiens*] (10 pages) and printout of sequence revision history (2 pages), from NCBI web site at www.ncbi.nlm.nih.gov (printed Jan. 20, 2008).

* cited by examiner

SEQUENCE LISTING

```
<160> NUMBER OF SEQ ID NOS: 5

<210> SEQ ID NO 1
<211> LENGTH: 5
<212> TYPE: PRT
<213> ORGANISM: Homo sapiens

<400> SEQUENCE: 1

Glu Ile Leu Asp Val
1               5

<210> SEQ ID NO 2
<211> LENGTH: 20
<212> TYPE: DNA
<213> ORGANISM: Artificial Sequence
<220> FEATURE:
<223> OTHER INFORMATION: antisense sequence

<400> SEQUENCE: 2
cttcccaagc catgcgctct                                                  20

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
tcgcttccca agccatgcgc                                                  20

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
gcctcgcttc ccaagccatg                                                  20

<210> SEQ ID NO 5
<211> LENGTH: 10
<212> TYPE: PRT
<213> ORGANISM: Artificial Sequence
<220> FEATURE:
<223> OTHER INFORMATION: RGD-4C

<400> SEQUENCE: 5

Ala Cys Asp Cys Arg Gly Asp Cys Phe Cys
1               5                   10
```

TREATMENT OF OCULAR DISORDERS

CROSS-REFERENCE TO RELATED APPLICATION

The present application claims priority to and the benefit of U.S. Ser. No. 60/547,156, filed on Feb. 23, 2004, the entirety of which is incorporated herein by reference.

FIELD OF THE INVENTION

The present invention relates generally to the field of intraocular disorders. More particularly, the invention relates to methods for treating such disorders using a Very late Antigen-4 (VLA-4) antagonist.

BACKGROUND

There are a variety of chronic ocular disorders, which, if untreated, may lead to partial or even complete vision loss. One prominent chronic ocular disorder is age-related macular degeneration, which is the leading cause of blindness amongst elderly Americans affecting a third of patients aged 75 years and older (Fine et al. (2000) NEW ENGL. J. MED. 342: 483-492). There are two forms of age-related macular degeneration, a wet form, which is associated with the formation of neovasculature in the choroid (also known as the neovascular form of age-related macular degeneration), and a dry form, which is not associated with the formation of choroidal neovasculaturization. The wet form accounts for approximately 90% of the severe vision loss associated with age-related macular degeneration.

Currently, treatment of the dry form of age-related macular degeneration includes administration of antioxidant vitamins and/or zinc. Treatment of the wet form of age-related macular degeneration, however, has proved to be more difficult. Currently, two separate methods have been approved in the United States of America for treating the wet form of age-related macular degeneration. These include laser photocoagulation and photodynamic therapy using a benzoporphyrin derivative photosensitizer. During laser photocoagulation, thermal laser light is used to heat and photocoagulate the neovasculature of the choroid. A problem associated with this approach is that the laser light must pass through the photoreceptor cells of the retina in order to photocoagulate the blood vessels in the underlying choroid. As a result, this treatment destroys the photoreceptor cells of the retina creating blind spots with associated vision loss. During photodynamic therapy, a benzoporphyrin derivative photosensitizer is administered to the individual to be treated. Once the photosensitizer accumulates in the choroidal neovasculature, nonthermal light from a laser is applied to the region to be treated, which activates the photosensitizer in that region. The activated photosensitizer generates free radicals that damage the vasculature in the vicinity of the photosensitizer (see, U.S. Pat. Nos. 5,798,349 and 6,225,303). This approach is more selective than laser photocoagulation and is less likely to result in blind spots. Under certain circumstances, this treatment has been found to restore vision in patients afflicted with the disorder (see, U.S. Pat. Nos. 5,756,541 and 5,910,510).

Another prominent chronic ocular disorder is uveitis. Uveitis is an inflammatory eye disorder and includes inflammation of the uveal tract, the vascular coat of the eye composed of the iris, ciliary body and choroid. While the ultimate goal of inflammation is to repair the initial cause of cell injury, inflammation can also cause harm to cells. This harm is thought to be caused by leukocytes which migrate from the microcirculation and accumulate and secrete cytokines at the site of accumulation. Among the complications associated with the inflammatory process in uveitis are glaucoma, lens opacification, retinal detachments and cystoid macular edema. All these can cause permanent vision loss.

Available treatments for uveitis are limited. Corticosteroids are the main drugs used for its treatment but they have numerous ocular (cataract and secondary glaucoma) and non-ocular adverse effects. Prolonged systemic steroid use can suppress musculoskeletal growth, cause impaired wound healing and result in increased susceptibility to infections. Cycloplegics are used for the alleviation of pain but can have adverse effects including photophobia and blurred vision. Thus, there is still an ongoing need for methods of preventing the onset of chronic ocular disorders, and once established, the treatment of such a disorder.

SUMMARY OF THE INVENTION

The present invention is based, in part, upon the finding that Very Late Antigen-4 (VLA-4) antagonists can be used in the treatment of certain ocular disorders.

In one aspect, the invention features a method of treating an intraocular disorder in a mammal, for example, a human. The method includes administering to the mammal a VLA-4 antagonist, such as a protein that binds specifically to VLA-4, or a nucleic acid that binds specifically to VLA-4, in an amount sufficient to ameliorate the symptoms of the disorder. In one embodiment, the protein is an antibody. In another embodiment, the nucleic acid is an aptamer. The antagonist can interfere with the binding of VLA-4 to its congnate VLA-4 receptor. The method also includes administering to the mammal a VLA-4 antagonist that inhibits or otherwise reduces the activity of VLA-4, for example, by inhibiting or reducing the ability of VLA-4 to bind specifically to its cognate receptor.

Exemplary intraocular disorders include without limitation, age-related macular degeneration, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy, thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome), retinal vascular disease (for example, diabetic retinopathy, Coat's disease and retinal arterial macroaneurysm), retinal artery occlusions, retinal vein occlusions, retinopathy of prematurity, retinitis pigmentosa, familial exudative vitreoretinopathy (FEVR), idiopathic polypoidal choroidal vasculopathy, epiretinal macular membranes and cataracts. Preferably, the intraocular disorder is an inflammatory intraocular disorder.

In another aspect, the invention features a method of treating age-related macular degeneration in a mammal, such as a human. The method includes administering to the mammal a VLA-4 antagonist in an amount sufficient to treat age-related macular degeneration. The antagonist can be a protein such as an antibody that binds specifically to VLA-4 or a nucleic acid such as an aptamer that binds specifically to VLA-4. In one embodiment, the age-related macular degeneration is the neovascular form of macular degeneration.

The antagonist as described above can be administered by any method known in the art, for example, parenterally or systemically. In one embodiment, the antagonist is administered locally to an eye of the mammal afflicted with the disorder.

In another aspect, the invention features a method of treating a disorder having unwanted choroidal neovasculature in a mammal, such as a human. The method includes the steps of: (a) administering to the mammal a photosensitizer in an amount sufficient to localize in the neovasculature; (b) administering to the mammal a therapeutically effective amount of a VLA-4 antagonist; and (c) irradiating the neovasculature with light from a laser thereby activating the photosensitizer present in the choroidal neovasculature. As a result, the treatment occludes the unwanted neovasculature in the mammal. In one embodiment, the photosensitizer is an amino acid derivative, an azo dye, a xanthene derivative, a chlorin, a tetrapyrrole derivative, or a phthalocyanine. For example, the photosensitizer is a lutetium texaphyrin, a benzoporphyrin, a benzoporphyrin derivative, a hematoporphyrin, or a hematoporphyrin derivative. The photosensitizer can include a targeting moiety that binds preferentially to endothelial cells of the neovasculature. The targeting moiety can be a peptide such as an α-vβ integrin, a vascular endothelial growth factor receptor, or a vascular cell adhesion molecule. In one embodiment, the VLA-4 antagonist is a protein such as an antibody that binds specifically to VLA-4 or is a nucleic acid such as an aptamer that binds specifically to VLA-4. The disorder can be any disorder having unwanted choroidal neovasculature such as age-related macular degeneration. The VLA-4 antagonist can administered to the mammal prior to, concurrent with, or subsequent to administration of the photosensitizer.

The foregoing aspects and embodiments of the invention may be more fully understood by reference to the detailed description and claims.

DETAILED DESCRIPTION OF THE INVENTION

VLA-4 is expressed on the cell surface of leukocytes and is understood to exert its biological activity by binding to its cognate receptor, the vascular cell adhesion molecule (VCAM), which is present on the cell surface of endothelial cells. It has been found that adhesion of leukocytes to the vascular wall can cause damage to the tissue to which it binds and the surrounding cells and tissues. The present invention is based, in part, on the finding that by blocking VLA-4 activity or expression, eye diseases which involve the adherence of leukocytes to the endotheluim can be treated. Accordingly, the invention relates to a treatment that includes the prevention, slowing or stopping of an ocular disorder by administering VLA-4 antagonists, e.g., antibodies to VLA-4. The present invention provides advantages over the current methods of treating inflammatory ocular disorders. For example, current methods involve the administration of steroids which are known to have adverse effects such as increased intraocular pressure, delayed wound healing or lead to the development of cataracts. In contrast, the mechanism of action of VLA-4 inhibitors is very specific. Moreover, VLA-4 is not expressed on neutrophils and therefore therapy directed against VLA-4 has the advantage of not interfering with neutrophil recruitment and defense against infection.

Intraocular disorders which can be treated using VLA-4 antagonists include without limitation, age-related macular degeneration, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy, thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome), retinal vascular disease (for example, diabetic retinopathy, Coat's disease and retinal arterial macroaneurysm), retinal artery occlusions, retinal vein occlusions, retinopathy of prematurity, retinitis pigmentosa, familial exudative vitreoretinopathy (FEVR), idiopathic polypoidal choroidal vasculopathy, epiretinal macular membranes and cataracts. Preferably, the intraocular disorder is an inflammatory intraocular disorder.

VLA-4 Antagonists

VLA-4 antagonists useful in the present invention include molecules which can inhibit or reduce VLA-4 expression and/or activity. For example, a VLA-4 antagonist is a molecule that includes one or more of the following properties: (1) binds preferentially to a VLA-4 molecule on the surface of a VLA-4 bearing cell to disrupt or inhibit a VLA-4/VLA-4 ligand interaction, e.g., the VLA-4/VCAM-1 interaction; (2) binds preferentially to a VLA-4 molecule on the surface of a VLA-4 bearing cell to modify, and preferably to inhibit, transduction of VLA-4-mediated signaling, e.g., VLA-4/VCAM-1-mediated signaling; (3) binds preferentially to a VLA-4 ligand, e.g., VCAM-1 or fibronectin, to disrupt or inhibit the VLA-4/VLA-4-ligand interaction; and (4) binds preferentially to a VLA-4-ligand, e.g., VCAM-1 or fibronectin, to modify, and preferably to inhibit, transduction of VLA-4-ligand mediated VLA-4 signaling, e.g., VCAM-1-mediated VLA-4 signaling. The VLA-4 antagonist can bind the alpha-4 chain of VLA-4, the beta-1 chain of VLA-4 or both the alpha-4 and beta-1 chains of VLA-4 to block or inhibit VLA-4 mediated binding or otherwise modulate VLA-4 function, e.g., by blocking or inhibiting VLA-4-ligand mediated VLA-4 signal transduction.

VLA-4 antagonists include but are not limited to proteins (which include, polypeptides and small peptides), peptide mimetics, carbohydrates, nucleic acids (for example, deoxyribonucleic acids or ribonucleic acids) and other small molecules capable of blocking VLA-4 activity, e.g., by binding a VLA-4 molecule on the surface of VLA-4-bearing cells or by binding to a VCAM-1 molecule on the surface of VCAM-1 bearing cells.

VLA-4 antagonists include soluble forms of proteins which bind VLA-4, e.g., the natural binding proteins for VLA-4. These binding proteins include soluble VCAM-1 or VCAM-1 peptides, VCAM-1 fusion proteins, bifunctional VCAM-1/Ig fusion proteins, anti-VLA-4 antibodies, fibronectin, fibronectin with an alternatively spliced non-type III connecting segment, and fibronectin peptides containing the amino acid sequence EILDV (SEQ ID NO: 1) or a similar conservatively substituted amino acid sequence. These binding proteins may act by competing with VLA-4 for binding to the VLA-4 receptor or by otherwise altering VLA-4 function. For example, a soluble form of VCAM-1 or a fragment thereof may be administered to bind VLA-4, and preferably compete for a VLA-4 binding site, thereby leading to effects similar to the administration of VLA-4 antibodies. Soluble VCAM-1 fusion proteins can be used in the methods described herein. For example, VCAM-1, or a fragment thereof, which is capable of binding to VLA-4 molecule on the surface of VLA-4 bearing cells, e.g., a fragment containing the two N-terminal domains of VCAM-1, can be fused to a second peptide, e.g., a peptide which increases the solubility or the in vivo life time of the VCAM-1 moiety. The second peptide can be a fragment of a soluble peptide, preferably a human peptide, more preferably a plasma protein, or a member of the immunoglobulin superfamily. In one example, the second peptide is IgG or a portion or fragment thereof, e.g., a human IgG1 heavy chain constant region.

VLA-4 antagonists also include antibodies. Antibodies include, for example, intact antibodies, for example, polyclonal or monoclonal antibodies, antigen binding fragments thereof, for example, Fab, Fab', (Fab')$_2$ and Fv antibody fragments, and biosynthetic antibody binding sites, for example, single chain Fv molecules as described in U.S. Pat. Nos. 5,091,513 and 5,132,405. In one embodiment, the VLA-4 antagonist is a monoclonal antibody capable of binding VLA-4 or VCAM-1 in a manner to prevent VLA-4 from binding to and/or interacting with VCAM-1. The production of monoclonal antibodies is well known in the art and, therefore, is not described in detail herein. Briefly, an immortal cell line (typically myeloma cells) is fused to lymphocytes (typically splenocytes) harvested from a mammal immunized with a given antigen, e.g., VLA-4. The culture supernatants of the resulting hybridoma cells then are screened for antibodies that preferentially bind the antigen, for example, with a binding affinity with greater than $10^5$ $M^{-1}$, more preferably greater than $10^7$ $M^{-1}$.

Several mouse anti-VLA-4 monoclonal antibodies such as HP1/2 and other anti-VLA-4 antibodies (e.g., mAb HP2/1, HP2/4, L25, P4C2, P4G9) have been described previously (see, for example, Pulido et al. (1991) J. BIOL. CHEM. 266(16): 10241-5 and Fryer et al. (1997) J. CLIN. INVEST. 99: 2036-2044). Human monoclonal antibodies that bind preferentially to VLA-4 can also be used in the practice of the invention. These may be prepared using in vitro-primed human splenocytes, as described by Boerner et al. (1991) J. IMMUNOL. 147: 86-95.

Other useful anti-VLA-4 antibodies include chimeric recombinant and humanized recombinant antibodies. The starting material for the preparation of chimeric (for example, murine immunoglobulin variable regions linked to human immunoglobulin constant regions) and humanized anti-VLA-4 antibodies may be a murine monoclonal anti-VLA-4 antibody either available commercially (e.g., the HP2/1 antibody available from Amac International, Inc., Westbrook, Me.) or prepared using principles known in the art. For example, the variable regions of the heavy and light chains of the HP1/2 anti-VLA-4 antibody can be cloned, sequenced and expressed in combination with constant regions of human immunoglobulin heavy and light chains. The resulting chimeric HP1/2 antibody preferably has binding specificity and potency comparable to the murine HP 1/2 antibody but with fewer antigenic sites than the contact murine HP1/2 antibody. Commercially available humanized VLA-4 antibodies are available, for example, from BiogenIDEC, Inc. (Cambridge, Mass.), and a commercially available mouse anti-rat monoclonal antibody, clone TA-2, is available from Associates of Cape Cod (Cape Cod, Mass.).

In addition, the VLA-4 antagonists may include a nucleic acid molecule or a nucleic acid mimetic. The mode of action of these types of antagonists may vary. For example, it is contemplated that certain nucleic acid molecules and nucleic acid mimetics may exert their effect through antisense-type technology while others may exert their effect through aptamer-type technology while others may exert their effect through RNAi technology.

In one embodiment, useful nucleic acids include anti-VLA-4 aptamers and anti-VCAM-1 aptamers. The anti-VLA-4 aptamer has a tertiary structure that permits it to bind preferentially to a VLA-4 molecule. The anti-VCAM-1 aptamer has a tertiary structure that permits it to bind preferentially to a VCAM-1 molecule. Methods for identifying suitable aptamers, for example, via systematic evolution of ligands by exponential enrichment (SELEX), are known in the art and are described, for example, in Ruckman et al. (1998) J. BIOL. CHEM. 273: 20556-20567; Costantino et al. (1998) J. PHARM. SCI. 87: 1412-1420.

Other useful anti-VLA-4 nucleic acid antagonists include antisense oligonucleotides. Exemplary antisense oligonucleotides that prevent or reduce the expression of VLA-4 have been described in the art, for example, in U.S. Pat. No. 6,258, 790, and can include for example, cttcccaagc catgcgctct (SEQ ID NO: 2), tcgcttccca agccatgcgc (SEQ ID NO: 3) or gcctcgcttc ccaagccatg (SEQ ID NO: 4). To the extent RNAi is used, double stranded RNA (dsRNA) having one strand identical (or substantially identical) to the target mRNA sequence is introduced to a cell. The dsRNA is cleaved into small interfering RNAs (siRNAs) in the cell, and the siRNAs interact with the RNA induced silencing complex to degrade the target mRNA, ultimately destroying production of a desired protein.

Alternatively, VLA-4 gene expression can be inhibited by using nucleotide sequences complementary to a regulatory region of the VLA-4 gene (e.g., the VLA-4 promoter and/or a enhancer) to form triple helical structures that prevent transcription of the VLA-4 gene in target cells. See generally, Helene (1991) ANTICANCER DRUG DES. 6(6): 569-84; Helene et al. (1992) ANN. NY ACAD. SCI. 660: 27-36; and Maher (1992) BIOESSAYS 14(12): 807-15.

In another embodiment, the antisense sequences may be modified at a base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) BIOORG. MED. CHEM. 4(1):5-23). Peptidyl nucleic acids have been shown to hybridize specifically to DNA and RNA under conditions of low ionic strength.

Small molecules such as oligosaccharides that mimic the VCAM binding domain of VLA-4 and bind VCAM may also be employed. Exemplary small molecules include phosphodiesterase-4 inhibitors, OMePUPA-V ((R)—N—[[4-[[(2-methylphenylamino)carbonyl]amino]phenyl]acetyl]-L-prolyl-3-methyl)-beta-Alanine), benzyl compounds or other molecules such as those disclosed in U.S. Pat. Nos. 6,686, 350, 6,685,617, 6,586,602, 6,583,139, and 6,559,127.

The ability of an antagonist of interest to block VLA-4 activity can be determined, for example, by using one or more of the numerous in vitro and in vivo assays known in the art. For example, some assays determine the concentration of an antagonist required to block the binding of VLA-4-expressing cells (for example, Ramos cells, Jurkat cells, A375 melanoma cells, as well as human peripheral blood lymphocytes (PBL)) to fibronectin or VCAM-1 coated plates. For example, once the wells of a microtiter plate are coated with either fibronectin or soluble VCAM-1, varying concentrations of the test antagonist then are added together with appropriately labeled VLA-4-expressing cells. Alternatively, the test antagonist may be added first and allowed to incubate with the coated wells prior to the addition of the labeled VLA-4-expressing cells. The cells are incubated in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

Alternatively, the VLA-4 antagonist can be assessed for its ability to inhibit VLA-4 activity using an in vitro adhesion assay as described in Barouch et al. (2000) INVEST. OPHTHALMOL. VIS. SCI. 41: 1153-1158. Briefly, endothelial cells are grown in confluence on 96-well plates and stimulated for 24 hours with lipopolysacharide (LPS). Leukocytes isolated from peripheral blood are incubated with a fluorescent marker for 10 minutes. The fluorescently labeled leukocytes then are incubated alone or with a saturating concentration of monoclonal antibodies (e.g., an anti-VLA-4 antibody). The leukocytes then are washed and incubated with the endothelial cells for 10 minutes at 37° C. Nonadherent cells are removed and the contents of the well lysed to determine the amount of fluorescence of the adhered cells.

Once VLA-4-specific antagonists have been identified in vitro, they may be further characterized using in vivo assays. For example, the efficacy of the antagonist to prevent the development of endotoxin induced uveitis in rats can be performed as described in Example 1.

Photodynamic Therapy (PDT)

The invention also relates to a PDT-based method for treating ocular disorders characterized as having unwanted choroidal neovasculature (CNV). Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases.

The method of the invention relates to a PDT-based method of treating unwanted target CNV. The method requires administration of: (i) a photosensitizer to a mammal in need of such treatment in an amount sufficient to permit an effective amount (i.e., an amount sufficient to facilitate PDT) of the photosensitizer to localize in the target CNV, and (ii) an effective amount of a VLA-4 antagonist, as described above, prior to, concurrent with, or subsequent to administration of the photosensitizer. After administration of the photosensitizer and the VLA-4 antagonist, the CNV is then irradiated with laser light under conditions such that the light is absorbed by the photosensitizer. The photosensitizer, when activated by the light, generates singlet oxygen and free radicals, for example, reactive oxygen species, that result in damage to surrounding tissue. For example, PDT-induced damage of endothelial cells results in platelet adhesion and degranulation, leading to stasis and aggregration of blood cells and vascular occlusion. Optionally, the method can include: (i) administering an anti-angiogenic factor such as angiostatin, endostatin or pigment epithelium-derived growth factor to the mammal prior to or concurrent with administration of the photosensitizer, (ii) administering a neuroprotective agent, for example, an apoptosis inhibitor, such as a caspase inhibitor, for example, one or more of a caspase 3 inhibitor, a caspase 7 inhibitor, and a caspase 9 inhibitor prior to, concurrent with, or after administration of the photosensitizer, (iii) using a photosensitizer with a targeting molecule that targets the photosensitizer to the CNV, or (iv) a combination of any of the foregoing.

It is contemplated that a variety of photosensitizers useful in PDT may be useful in the practice of the invention and include, for example, amino acid derivatives, azo dyes, xanthene derivatives, chlorins, tetrapyrrole derivatives, phthalocyanines, and assorted other photo sensitizers.

Amino acid derivatives include, for example, 5-aminolevulinic acid (Berg et al. (1997) PHOTOCHEM. PHOTOBIOL 65: 403-409; El-Far et al. (1985) CELL. BIOCHEM. FUNCTION 3, 115-119). Azo dyes, include, for example, Sudan I, Sudan II, Sudan III, Sudan IV, Sudan Black, Disperse Orange, Disperse Red, Oil Red O, Trypan Blue, Congo Red, β-carotene (Mosky et al. (1984) EXP. RES. 155, 389-396). Xanthene derivatives, include, for example, rose bengal.

Chlorins include, for example, lysyl chlorin p6 (Berg et al. (1997) supra) and etiobenzochlorin (Berg et al. (1997) supra), 5, 10, 15, 20-tetra (m-hydroxyphenyl) chlorin (M-THPC), N-aspartyl chlorin e6 (Dougherty et al. (1998) J. NATL. CANCER INST. 90: 889-905), and bacteriochlorin (Korbelik et al. (1992) J. PHOTOCHEM. PHOTOBIOL. 12: 107-119).

Tetrapyrrole derivatives include, for example, lutetium texaphrin (Lu-Tex, PCI-0123) (Dougherty et al. (1998) supra, Young et al. (1996) PHOTOCHEM. PHOTOBIOL. 63: 892-897); benzoporphyrin derivative (BPD) (U.S. Pat. Nos. 5,171,749, 5,214,036, 5,283,255, and 5,798,349, Jori et al. (1990) LASERS MED. SCI. 5, 115-120), benzoporphyrin derivative mono acid (BPD-MA) (U.S. Pat. Nos. 5,171,749, 5,214,036, 5,283,255, and 5,798,349, Berg et al. (1997) supra, Dougherty et al. (1998) supra), hematoporphyrin (Hp) (Jori et al. (1990) supra), hematoporphyrin derivatives (HpD) (Berg et al. (1997) supra, West et al. (1990) IN. J. RADIAT. BIOL. 58: 145-156), porfimer sodium or Photofrin (PHP)(Berg et al. (1997) supra), Photofrin II (PII)(He et al. (1994) PHOTOCHEM. PHOTOBIOL. 59: 468-473), protoporphyrin IX (PpIX) (Dougherty et al. (1998) supra, He et al. (1994) supra), meso-tetra (4-carboxyphenyl) porphine (TCPP)(Musser et al. (1982) RES. COMMUN. CHEM. PATHOL. PHARMACOL. 2, 251-259), meso-tetra (4-sulfonatophenyl)porphine (TSPP) (Musser et al. (1982) supra), uroporphyrin I (UROP-I)(El-Far et al. (1985) CELL. BIOCHEM. FUNCTION 3, 115-119), uroporphyrin III (UROP-III)(El-Far et al. (1985) supra), tin ethyl etiopurpurin (SnET2), (Dougherty et al. (1998) supra 90: 889-905) and 13, 17-bis[1-carboxypropionyl] carbamoylethyl-8-etheny-2-hydroxy-3-hydroxyiminoethyliden e-2,7,12,18-tetranethyl 6 porphyrin sodium (ATX-S10(Na)) Mori et al. (2000) JPN. J. CANCER RES. 91: 753-759, Obana et al. (2000) ARCH. OPHTHALMOL. 118: 650-658, Obana et al. (1999) LASERS SURG. MED. 24: 209-222).

Phthalocyanines include, for example, chloroaluminum phthalocyanine (AlPcCl)(Rerko et al. (1992) PHOTOCHEM. PHOTOBIOL. 55, 75-80), aluminum phthalocyanine with 2-4 sulfonate groups (AlPcS$_{2-4}$)(Berg et al. (1997) supra, Glassberg et al. (1991) LASERS SURG. MED. 11, 432-439), chloroaluminum sulfonated phthalocyanine (CASPc)(Roberts et al. (1991) J. NATL. CANCER INST. 83, 18-32), phthalocyanine (PC) (Jori et al. (1990) supra), silicon phthalocyanine (Pc4)(He et al. (1998) PHOTOCHEM. PHOTOBIOL. 67: 720-728, Jori et al. (1990) supra), magnesium phthalocyanine ($Mg^{2+}$-PC) (Jori et al. (1990) supra), zinc phthalocyanine (ZnPC) (Berg et al. (1997) supra). Other photosensitizers include, for example, thionin, toluidine blue, neutral red and azure c.

However, useful photosensitizers, include, for example, Lutetium Texaphyrin (Lu-Tex), a new generation photosensitizer having favorable clinical properties because its absorption at about 730 nm permits deep tissue penetration and rapid clearance. Lu Tex is available from Alcon Laboratories, Fort Worth, Tex. Other useful photosensitizers, include benzoporhyrin and benzoporphyrin derivatives, for example, BPD-MA and BPD-DA, available from QLT, Inc., Vancouver, Canada.

The photosensitizer preferably is formulated into a delivery system that delivers high concentrations of the photosensitizer to the CNV. Such formulations may include, for example, the combination of a photosensitizer with a carrier that delivers higher concentrations of the photosensitizer to CNV and/or coupling the photosensitizer to a specific binding ligand that binds preferentially to a specific cell surface component of the CNV.

In one preferred embodiment, the photosensitizer can be combined with a lipid based carrier. For example, liposomal formulations have been found to be particularly effective at delivering the photosensitizer, green porphyrin, and more particularly BPD-MA to the low-density lipoprotein component of plasma, which in turn acts as a carrier to deliver the photosensitizer more effectively to the CNV. Increased numbers of LDL receptors have been shown to be associated with CNV, and by increasing the partitioning of the photosenstizer into the lipoprotein phase of the blood, it may be delivered more efficiently to the CNV. Certain photosensitizers, for example, green porphyrins, and in particular BPD-MA, interact strongly with lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins formulated as lipocomplexes, including liposomes, are described, for example, in U.S. Pat. Nos. 5,214,036, 5,707,608 and 5,798,349. Liposomal formulations of green porphyrin can be obtained from QLT, Inc., Vancouver, Canada. It is contemplated that certain other photosensitizers may likewise be formulated with lipid carriers, for example, liposomes or LDL, to deliver the photosensitizer to CNV.

Furthermore, the photosensitizer can be coupled to a specific binding ligand that binds preferentially to a cell surface component of the CNV, for example, neovascular endothelial homing motif. It appears that a variety of cell surface ligands are expressed at higher levels in new blood vessels relative to other cells or tissues.

Endothelial cells in new blood vessels express several proteins that are absent or barely detectable in established blood vessels (Folkman (1995) NATURE MEDICINE 1: 27-31), and include integrins (Brooks et al. (1994) SCIENCE 264: 569-571; Friedlander et al. (1995) SCIENCE 270: 1500-1502) and receptors for certain angiogenic factors like vascular endothelial growth factor (VEGF). In vivo selection of phage peptide libraries have also identified peptides expressed by the vasculature that are organ-specific, implying that many tissues have vascular "addresses" (Pasqualini et al. (1996) NATURE 380: 364-366). It is contemplated that a suitable targeting moiety can direct a photosensitizer to the CNV endothelium thereby increasing the efficacy and lowering the toxicity of PDT.

Several targeting molecules may be used to target photosensitizers to the neovascular endothelium. For example, α-v integrins, in particular α-v β3 and α-v β5, appear to be expressed in ocular neovascular tissue, in both clinical specimens and experimental models (Corjay et al. (1997) INVEST. OPHTHALMOL. VIS. SCI. 38, S965; Friedlander et al. (1995) supra). Accordingly, molecules that preferentially bind α-v integrins can be used to target the photosensitizer to CNV. For example, cyclic peptide antagonists of these integrins have been used to inhibit neovascularization in experimental models (Friedlander et al. (1996) PROC. NATL. ACAD. SCI. USA 93: 9764-9769). A peptide motif having an amino acid sequence, in an N- to C-terminal direction, ACDCRGDCFC (SEQ ID NO: 5)—also know as RGD-4C—has been identified that selectively binds to human α-v integrins and accumulates in tumor neovasculature more effectively than other angiogenesis targeting peptides (Arap et al. (1998) NATURE 279: 377-380; Ellerby et al. (1999) NATURE MEDICINE 5: 1032-1038). Angiostatin may also be used as a targeting molecule for the photosensitizer. Studies have shown, for example, that angiostatin binds specifically to ATP synthase disposed on the surface of human endothelial cells (Moser et al. (1999) PROC. NALT. ACAD. SCI. USA 96: 2811-2816).

Another potential targeting molecule is an antibody for vascular endothelial growth factor receptor (VEGF-2R). Clinical and experimental evidence strongly supports a role for VEGF in ocular neovascularization, particularly ischemia-associated neovascularization (Adamis et al. (1996) ARCH. OPHTHALMOL. 114: 66-71; Tolentino et al. (1996) ARCH. OPHTHALMOL. 114: 964-970; Tolentino et al. (1996) OPHTHALMOLOGY 103: 1820-1828). Antibodies to the VEGF receptor (VEGFR-2 also known as KDR) may also bind preferentially to neovascular endothelium. A useful targeting molecule includes the recombinant humanized anti-VEGF monoclonal antibody fragment known as rhuFab available from Genentech, Vacaville, Calif.

The targeting molecule may be synthesized using methodologies known and used in the art. For example, proteins and peptides may be synthesized using conventional synthetic peptide chemistries or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press. Once created, the targeting agent may be coupled to the photosensitizer using standard coupling chemistries, using, for example, conventional cross linking reagents, for example, heterobifunctional cross linking reagents available, for example, from Pierce, Rockford, Ill.

Formulation and Administration of VLA-4 Antagonists

The type and dosage of the VLA-4 antagonist administered may depend upon various factors including, for example, the age, weight, gender, and health of the individual to be treated, as well as the type and/or severity of the particular disorder to be treated. The formulations, both for veterinary and for human medical use, typically include an antagonist in association with a pharmaceutically acceptable carrier or excipient.

The carrier should be acceptable in the sense of being compatible with the other ingredients of the formulations and not deleterious to the recipient. Pharmaceutically acceptable carriers, in this regard, are intended to include any and all solvents, dispersion media, coatings, isotonic and absorption delaying agents, and the like, that are compatible with pharmaceutical administration. The use of such media and agents for pharmaceutically active substances is known in the art. Supplementary active compounds (identified or designed according to the invention and/or known in the art) also can be incorporated into the formulations. The formulations may conveniently be presented in dosage unit form and may be prepared by any of the methods well known in the art of pharmacy/microbiology. In general, some formulations are prepared by bringing the active molecule into association with a liquid carrier or a finely divided solid carrier or both, and then, if necessary, shaping the product into the desired formulation.

A pharmaceutical composition of the invention should be formulated to be compatible with its intended route of administration. Examples of routes of administration include local or systemic routes. Local routes include, for example, topical application to the eye, or intraorbital, periorbital, sub-tenons, intravitreal and transscleral delivery. Systemic routes include, for example, oral or parenteral routes, or alternatively via intramuscular, intravenous, intradermal, inhalation, transdermal (topical), transmucosal, and rectal routes.

Formulations suitable for oral or parenteral administration may be in the form of discrete units such as capsules, gelatin capsules, sachets, tablets, troches, or lozenges, each containing a predetermined amount of the active agent; a powder or granular composition; a solution or a suspension in an aqueous liquid or non-aqueous liquid; or an oil-in-water emulsion or a water-in-oil emulsion. Formulations suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL castor oil (BASF, Parsippany, N.J.) or phosphate buffered saline (PBS). Sterile injectable solutions can be prepared by incorporating the active compound in the required amount in an appropriate solvent with one or a combination of ingredients enumerated above, as required, followed by filter sterilization. Formulations suitable for intra-articular administration may be in the form of a sterile aqueous preparation of the drug which may be in microcrystalline form, for example, in the form of an aqueous microcrystalline suspension. Liposomal formulations or biodegradable polymer systems may also be used to present the drug for both intra-articular and ophthalmic administration. Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations.

In therapeutic uses for treating ocular disorders, the active ingredients typically are administered orally, parenterally and/or topically at a dosage to obtain and maintain a concentration that is therapeutically effective in the eye. In certain circumstances, a therapeutically effective dose of the VLA-4 antagonist prevents or reduces the ability of VLA-4 to bind to its binding partner, for example, VCAM, and/or prevents or reduces the ability of VLA-4 to activate its binding partner, for example, VCAM. Generally, an effective amount of dosage of active molecule will be in the range of from about 0.1 mg/kg to about 100 mg/kg, optionally from about 1.0 mg/kg to about 50 mg/kg of body weight/day. The amount administered likely will depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, two to four times per day.

Formulation and Administration of Photosensitizers

Photosensitizers as described herein may be administered in any of a wide variety of ways, for example, orally, parenterally, or rectally. Parenteral administration, such as intravenous, intramuscular, or subcutaneous, is preferred. Intravenous injection is especially preferred. The dose of photosensitizer can vary widely depending on the tissue to be treated; the physical delivery system in which it is carried, such as in the form of liposomes; or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in PDT, and time interval between administration of the dose and the therapeutic irradiation. All of these parameters should be adjusted to produce significant damage to CNV without significant damage to the surrounding tissue.

Typically, the dose of photosensitizer used is within the range of from about 0.1 to about 20 mg/kg, preferably from about 0.15 to about 5.0 mg/kg, and even more preferably from about 0.25 to about 2.0 mg/kg. Furthermore, as the dosage of photosensitizer is reduced, for example, from about 2 to about 1 mg/kg in the case of green porphyrin or BPD-MA, the fluence required to close CNV may increase, for example, from about 50 to about 100 Joules/cm$^2$. Similar trends may be observed with the other photosensitizers discussed herein.

After the photosensitizer has been administered, the CNV is irradiated at a wavelength typically around the maximum absorbance of the photosensitizer, usually in the range from about 550 nm to about 750 mn. A wavelength in this range is especially preferred for enhanced penetration into bodily tissues. Preferred wavelengths used for certain photosensitizers include, for example, about 690 nm for benzoporphyrin derivative mono acid, about 630 nm for hematoporphyrin derivative, about 675 nm for chloro-aluminum sulfonated phthalocyanine, about 660 nm for tin ethyl etiopurpurin, about 730 nm for lutetium texaphyrin, about 670 nm for ATX-S10 (NA), about 665 nm for N-aspartyl chlorin e6, and about 650 nm for 5, 10, 15, 20-tetra (m-hydroxyphenyl) chlorin.

As a result of being irradiated, the photosensitizer in its triplet state is thought to interact with oxygen and other compounds to form reactive intermediates, such as singlet oxygen and reactive oxygen species, which can disrupt cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to the endothelial cells, with subsequent platelet adhesion, degranulation, and thrombus formation.

The fluence during the irradiating treatment can vary widely, depending on the type of photosensitizer used, the type of tissue, the depth of target tissue, and the amount of overlying fluid or blood. Fluences preferably vary from about 10 to about 400 Joules/cm$^2$ and more preferably vary from about 50 to about 200 Joules/cm$^2$. The irradiance varies typically from about 50 mW/cm$^2$ to about 1800 mW/cm$^2$, more preferably from about 100 mW/cm$^2$ to about 900 mW/cm$^2$, and most preferably in the range from about 150 mW/cm$^2$ to about 600 mW/cm$^2$. It is contemplated that for many practical applications, the irradiance will be within the range of about 300 mW/cm$^2$ to about 900 mW/cm$^2$. However, the use of higher irradiances may be selected as effective and having the advantage of shortening treatment times.

The time of light irradiation after administration of the photosensitizer may be important as one way of maximizing the selectivity of the treatment, thus minimizing damage to structures other than the target tissues. The optimum time following photosensitizer administration until light treatment can vary widely depending on the mode of administration, the form of administration such as in the form of liposomes or as a complex with LDL, and the type of target tissue. For example, benzoporphyrin derivative typically becomes present within the target neovasculature within one minute post administration and persists for about fifty minutes, lutetium texaphyrin typically becomes present within the target neovasculature within one minute post administration and persists for about twenty minutes, N-aspartyl chlorin e6 typically becomes present within the target neovasculature within one minute post administration and persists for about twenty minutes, and rose bengal typically becomes present in the target vasculature within one minute post administration and persists for about ten minutes.

Effective vascular closure generally occurs at times in the range of about one minute to about three hours following administration of the photosensitizer. However, as with green porphyrins, it is undesirable to perform the PDT within the first five minutes following administration to prevent undue damage to retinal vessels still containing relatively high concentrations of photosensitizer.

The efficacy of PDT may be monitored using conventional methodologies, for example, via fundus photography or angiography. Closure can usually be observed angiographically by hypofluorescence in the treated areas in the early angiographic frames. During the later angiographic frames, a corona of hyperfluorescence may begin to appear which then fills the treated area, possibly representing leakage from the adjacent choriocapillaris through damaged retinal pigment epithelium in the treated area. Large retinal vessels in the treated area typically perfuse following photodynamic therapy.

In light of the foregoing general discussion, the specific examples presented below are illustrative only and are not intended to limit the scope of the invention. Other generic and specific configurations will be apparent to those persons skilled in the art.

EXAMPLES

Example 1

USE of an Anti-VLA-4 Antibody in the Treatment of Uveitis

This example shows that it is possible to prevent the development of uveitis by administering an anti-VLA-4 antibody to a mammal at risk of developing uveitis.

Endotoxin induced uveitis was created in a Lewis rat by injecting lipopolysaccharide (LPS) into the footpad of the rat (see, Rosenbaum et al. (1980) NATURE 7: 611-3). Immediately after the LPS administration, the animals were randomized in two groups, which received either a single intraperitoneal injection of 5 mg/kg of a specific neutralizing mouse anti-rat VLA-4 antibody (n=11) or an isotype-matched IgG (n=13) (VLA-4 antibody was purchased from Associates of Cape Cod, Cape Cod, Mass. and the mouse anti-rat IgG1 was purchased from Southern Biotech, Inc, Alabama, US). Twenty-four hours after the induction of uveitis, the severity of uveitis was evaluated in vivo using slit-lamp biomicroscopy and by cell and protein measurement following aspiration of the aqueous fluid. Retinal leukocyte adhesion was quantified with FITC-lectin labeling as described in Joussen et al. (2003) INVEST. OPHTHAL. VIS. SCI. 44(5): 2184-91 and by counting of vitreous leukocytes in H&E-stained sections of paraffin-embedded eyes. Retinal vascular cell adhesion molecule-1 (VCAM-1) levels were evaluated by Western Blotting (Chen et al. (2002) KIDNEY INT. 61(2):414-24). Leukocytes from LPS-injected and control rats were isolated with a density gradient, and leukocyte adhesion to rat endothelial cells was quantified using a static in vitro adhesion assay.

When administered, the anti-VLA-4 antibody prevented all uveitis-induced inflammatory parameters. Clinical score and protein content in the aqueous fluid of the anti-VLA-4 antibody treated animals were decreased by 45% (p<0.001) and 21% (p<0.01), respectively, compared to the control rats. Retinal leukostasis decreased by 68% (p<0.001), and leukocyte accumulation in the vitreous body decreased by 75% (p<0.01) in the anti-VLA-4 antibody treated animals versus control eyes. Leukocytes derived from EIU animals showed increased adhesion to endothelial monolayers in vitro, which was effectively reduced by 70% with a VLA-4 blocking antibody (n=6, p<0.001). VCAM-1 expression in the retinas of control animals with uveitis was upregulated compared to normal controls.

The results show that VLA-4 blockade prevents the development of intraocular inflammation in an animal model of uveitis.

Example 2

Use of an Anti-VLA-4 Antibody in the Treatment of Diabetic Retinopathy

This example shows that by administering an anti-VLA-4 antibody to a mammal it is possible to block VLA-4 mediated leukostasis during early diabetic retinopathy.

Streptozotocin was administered to Long Evans rats to induce diabetes as described in Joussen et al. (2001) AM J. PATHOL. 158(1):147-152. The adhesive role of the integrin VLA-4 was tested in vivo using a specific neutralizing monoclonal antibody (mouse anti-rat VLA-4 antibody available from Associates of Cape Cod, Cape Cod, Mass.). The mouse anti-VLA-4 antibody was administered intraperitoneally at a concentration of 5 mg/kg or 1 mg/kg either 11 or 13 days after the induction of diabetes. The effect on retinal leukocyte adhesion was quantified 14 days after the induction of diabetes in a retinal flatmount via FITC-ConA lectin staining as described by Joussen et al. (2001) supra. The expression of VLA-4 on the surface of peripheral blood lymphocytes and monocytes from normal and two week diabetic rats was measured by Flow Cytometric analysis (Barouch et al. (2000) INVEST. OPHTHALMOL. VIS. SCI. 41: 1153-1158). The presence of VCAM-1 in diabetic retina was investigated by Western Blotting as described in Chen et al. (2002) KIDNEY INT. 61(2): 414-24.

The results showed that the in vivo intraperitoneal administration of anti-VLA-4 antibody at concentrations of 5 mg/kg and 1 mg/kg led to a statistically significant decrease of diabetic retinal leukostasis in two week diabetic animals. More specifically, the anti VLA-4 antibody, when given at a concentration of 5 mg/kg (n=18) led to an 82.5% (p<0.001) decrease in retinal leukocyte adhesion relative to control animals (n=9) that received 5 mg/kg of the non-immune IgG (mouse anti-rat IgG1, Southern Biotech, Inc). When the anti-VLA-4 antibody was administered at a concentration of 1 mg/kg (n=12) there was a 74% (p<0.001) decrease in retinal leukostasis relative to control animals (n=9) that received an equal dose of the non-immune IgG. VLA-4 was expressed on 74% of the peripheral lymphocytes-monocytes derived from the normal non-diabetic rats and on 95% of the cells from the diabetic rats.

These results show that VLA-4 blockade potently decreased leukostasis in the diabetic vasculature.

Example 3

Treatment of Choroidal Neovascularization Via Combination Therapy Using Photodynamic Therapy and VLA-4 Antagonist Therapy Cynomolgus monkeys weighing 3-4 kg are anesthetized with an intramuscular injection of ketamine hydrochloride (20 mg/kg), diazepam (1 mg/kg), and atropine (0.125 mg/kg), with a supplement of 5-6 mg/kg of ketamine hydrochloride as needed. For topical anesthesia, proparacaine (0.5%) is used. The pupils are dilated with 2.5% phenylephrine and 0.8% tropicamide.

Choroidal neovascularization is induced in the eyes of the monkeys using a modification of the Ryan model, in which burns are placed in the macula, causing breaks in Bruch's membrane, with a COHERENT ARGON DYE LASER 920 laser, Coherent Medical Laser, Palo Alto, Calif. (Ohkuma, H. et al. ARCH. OPHTHALMOL. (1983) 101: 1102-1110; Ryan, S. J. ARCH. OPHTHALMOL. (1982) 100: 1804-1809). Initially, a power of 300-700 mW for 0.1 seconds is used to form spots of about 100 µm, but improved rates of neovascularization can be obtained with 50 micron spots using a power of about 300-450 mW for 0.1 second.

The resulting choroidal neovascularizations are observed by (1) fundus photography (using a CANON FUNDUS CF-60Z camera, Lake Success, Long Island, N.Y.); (2) by fluorescein angiography (for example, by using about 0.1 ml/kg body weight of 10% sodium fluorescein via saphenous vein injection); and (3) histologic examination by light and electron microscopy.

Immediately before use, benzoporphyrin derivative-monoacid is dissolved in dimethyl sulfoxide (Aldrich Chemical Co., Inc., Milwaukee, Wis.) at a concentration of about 4 mg/ml. Dulbeccos phosphate buffered salt solution is then added to the stock to achieve a final BPD concentration of 0.8 mg/ml. Human low-density-lipoprotein (LDL) prepared from fresh frozen plasma is added at a ratio of 1:2.5 mg BPD-MA:LDL. The green porphyrin dye and dye solutions are protected from light at all times. After mixing, the dye preparation is incubated at 37° C. for 30 minutes prior to intravenous injection. The monkeys then are injected intravenously via a leg vein with 1-2 mg/kg of the BPD-MA complexed with LDL over a five-minute period, followed by a flush of 3-5 cm$^3$ of normal saline. Anti-VLA-4 antibody is also concurrently injected intravenously via a leg vein.

Following intravenous injection, the eyes of the monkeys are irradiated with 692 nm of light from an argon/dye laser (COHERENT 920, Coherent Medical Laser, Palo Alto, Calif.), using a COHERENT LDS-20 slit lamp (Coherent Medical Laser, Palo Alto, Calif.). The standard fiber is coupled to larger 400 µm silica optical fiber (Coherent Medical Laser, Palo Alto, Calif.) to allow larger treatment spots as desired.

The photodynamic irradiation treatments are carried out with a plano fundus contact lens (OGFA, Ocular Instruments, Inc., Bellvue, Mass.). The fluence at each treatment spot is 50, 75, 100 or 150 Joules/cm$^2$. Initially, the irradiance is set at 150 mW/cm$^2$ to avoid any thermal effect but, as the experiment proceeds, the irradiance can be increased to 300 mW/cm$^2$ or 600 mW/cm$^2$ to reduce the treatment duration time. The time interval between injection of the green porphyrin dye and the treatment irradiating step can range from about 1 to about 81 minutes.

"Dye only" controls, which are exposed to dye but not to laser light, are examined in the areas of normal retina/choroid. Areas of choroidal neovascularization are examined angiographically and histologically. Following photodynamic therapy, the monkeys are returned to an animal care facility. No attempt is made to occlude the animals' eyes, but the room in which they are housed is darkened overnight.

The condition of the choroidal neovasculature is followed by fundus photography, fluorescein angiography, and histologic examination. In particular, the eyes of the monkeys are examined by fluorescein angiography acutely and at 24 hours after the photodynamic therapy. In some cases, follow-up by fluorescein angiography is performed at 48 hours and at one week, until the eyes are harvested and the animals killed at the following time points: acutely, at 24 hours, 48 hours, and 8 days following photodynamic therapy. Animals are sacrificed with an intravenous injection of 25 mg/mg Nembutal.

It is contemplated that more choroidal neovascularization will be closed by photodynamic therapy in combination with the VLA-4 antagonist relative to photodynamic therapy alone.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating an intraocular disorder in a mammal, the method comprising:
administering to the mammal a Very Late Antigen-4 (VLA-4) antagonist comprising a protein that binds specifically to VLA-4 in an amount sufficient to treat the disorder, wherein the disorder is selected from the group consisting of uveitis, age-related macular degeneration, proliferative vitreoretinopathy, and diabetic retinopathy.

2. The method of claim 1, wherein the protein is an antibody.

3. The method of one of claims 1 or 2, wherein the disorder is uveitis.

4. The method of one of claims 1 or 2, wherein the disorder is proliferative vitreoretinopathy.

5. The method of one of claims 1 or 2, wherein the disorder is diabetic retinopathy.

6. The method of claim 1, wherein the disorder is age-related macular degeneration.

7. The method of claim 6, wherein the age-related macular degeneration is the neovascular form of macular degeneration.

8. The method of claim 1, wherein the mammal is a human.

9. The method of claim 1, wherein the antagonist is administered parenterally or systemically.

10. The method of claim 1, wherein the antagonist is administered locally to an eye of the mammal afflicted with the disorder.

11. The method of claim 1, wherein the antagonist interferes with the binding of VLA-4 to a VLA-4 ligand.

12. A method of treating an inflammatory intraocular disorder in a mammal, the method comprising:
administering to the mammal a VLA-4 antagonist comprising a protein that binds specifically to VLA-4 in an amount sufficient to treat the inflammatory intraocular disorder.

13. The method of claim 12, wherein the protein is an antibody.

14. The method of claim 12, wherein the mammal is a human.

15. The method of claim 12, wherein the antagonist is administered parenterally or systemically.

16. The method of claim 12, wherein the antagonist is administered locally to an eye of the mammal.

17. The method of claim 12, wherein the antagonist interferes with the binding of VLA-4 to a VLA-4 ligand.

18. A method of treating age-related macular degeneration in a mammal, the method comprising:
administering to the mammal a VLA-4 antagonist that binds specifically to VLA-4 in an amount sufficient to treat age-related macular degeneration, wherein the antagonist comprises an antibody that binds specifically to VLA-4.

19. The method of claim 18, wherein the age-related macular degeneration is the neovascular form of macular degeneration.

20. The method of claim 18, wherein the mammal is a human.

21. The method of claim 18, wherein the antagonist is administered parenterally or systemically.

22. The method of claim 18, wherein the antagonist is administered locally to an eye of the mammal.

23. A method of treating an intraocular disorder in a mammal, the method comprising:
administering to the mammal an antibody that binds specifically to VLA-4 in an amount sufficient to treat an intraocular disorder selected from the group consisting of age-related macular degeneration, proliferative vitreoretinopathy, uveitis and diabetic retinopathy.

24. The method of claim 23, wherein the intraocular disorder is uveitis.

25. The method of claim 23, wherein the intraocular disorder is diabetic retinopathy.

26. The method of claim 23, wherein the mammal is a human.

27. The method of claim 23, wherein the antibody is administered parenterally or systemically.

28. The method of claim 23, wherein the antibody is administered locally to an eye of the mammal afflicted with the disorder.

29. The method of claim 23, wherein the antibody interferes with the binding of VLA-4 to a VLA-4 ligand.

30. The method of claim 23, wherein the intraocular disorder is age-related macular degeneration.

31. The method of claim 30, wherein the age-related macular degeneration is the neovascular form of macular degeneration.

32. The method of claim 23, wherein the intraocular disorder is proliferative vitreoretinopathy.

33. A method for inhibiting leukostasis associated with an eye disorder in a mammal, the method comprising:
administering to the mammal a VLA-4 antagonist comprising a protein that binds specifically to VLA-4 in an amount sufficient to inhibit leukostasis.

34. The method of claim 33, wherein the protein is an antibody.

35. The method of claim 33, wherein the mammal is a human.

36. The method of claim 33, wherein the antagonist is administered parenterally or systemically.

37. The method of claim 33, wherein the antagonist is administered locally to an eye of the mammal.

38. The method of claim 33, wherein the antagonist interferes with the binding of VLA-4 to a VLA-4 ligand.

39. A method for inhibiting leukostasis associated with an eye disorder in a mammal, the method comprising:
administering to the mammal an antibody that binds specifically to VLA-4 in an amount sufficient to inhibit leukostasis.

40. The method of claim 39, wherein the mammal is a human.

41. The method of claim 39, wherein the antibody is administered parenterally or systemically.

42. The method of claim 39, wherein the antibody is administered locally to an eye of the mammal.

43. The method of claim 39, wherein the antibody interferes with the binding of VLA-4 to a VLA-4 ligand.

44. A method of treating an inflammatory intraocular disorder in a mammal, the method comprising:
administering to the mammal an antibody that binds specifically to VLA-4 in an amount sufficient to treat the inflammatory intraocular disorder.

45. The method of claim 44, wherein the mammal is a human.

46. The method of claim 44, wherein the antibody is administered parenterally or systemically.

47. The method of claim 44, wherein the antibody is administered locally to an eye of the mammal.

48. The method of claim 44, wherein the antibody interferes with the binding of VLA-4 to a VLA-4 ligand.

* * * * *